| United States Patent [19] | [11] Patent Number: 4,853,224 |
| Wong | [45] Date of Patent: Aug. 1, 1989 |

[54] BIODEGRADABLE OCULAR IMPLANTS

[75] Inventor: Vernon G. Wong, Sunnyvale, Calif.

[73] Assignee: Visionex, Sunnyvale, Calif.

[21] Appl. No.: 136,402

[22] Filed: Dec. 22, 1987

[51] Int. Cl.⁴ .............................................. A61F 2/00
[52] U.S. Cl. ..................................... 424/427; 424/423
[58] Field of Search ......................................... 424/427

[56] References Cited

U.S. PATENT DOCUMENTS

| 3,914,402 | 10/1975 | Shell | 424/428 |
| 3,986,510 | 11/1976 | Higuchi et al. | 424/428 |
| 4,001,388 | 1/1977 | Shell | 424/438 |
| 4,115,544 | 9/1978 | Shell | 424/428 |

*Primary Examiner*—Thurman K. Page
*Assistant Examiner*—Leon R. Horne
*Attorney, Agent, or Firm*—Bertram I. Rowland

[57] ABSTRACT

Microencapsulated drugs are employed for introduction into the chambers of the eye for therapeutic purposes. The administration of drugs is controlled and maintained for long periods of time, while ensuring the substantial absence of significant levels outside the site of administration.

12 Claims, No Drawings

BIODEGRADABLE OCULAR IMPLANTS

TECHNICAL FIELD

Biocompatible microencapsulated implants are provided for treatment of ocular diseases.

BACKGROUND OF THE INVENTION

The eye is fundamentally one of the most important organs during life. Because of aging, diseases and other factors which can adversely affect vision, the ability to maintain the health of the eye becomes all important. The leading cause of blindness is the inability in the treatment of eye diseases to introduce drugs or therapeutic agents into the eye. The exact mechanism or reason is not known, but certainly the blood eye barrier (as analogous to the blood brain barrier) may be an important factor. On the other hand, when a drug is injected into the eye, it quickly washes out or is depleted from within the eye into the general circulation. From the therapeutic standpoint, this may be as difficult as giving no drug at all. Because of this inherent difficulty of delivering drugs into the eye, successful medical treatment of ocular diseases is totally inadequate.

The need for a solution is even more pressing in that the cause of a number of ocular diseases have now been identified and many are amenable to treatment if a proper mode of therapeutic delivery is available. It is therefore of great interest to develop modes of treatment which obviate the limitations of present modes of therapy.

There has been a substantial resistance to introduce drugs directly into one or both chambers of the eye. The many uncertainties associated with the distribution of the drug, rate of release, binding to eye components, concentration by cells, rapid loss and/or inactivation, and the like, is discouraging for the efficacy of direct introduction.

RELEVANT LITERATURE

Heller (1), Biodegradable Polymers in Controlled Drug Delivery, In: CRC Critical Reviews in Therapeutic Drug Carrier Systems, Vol. 1, CRC Press, Boca Ratio, FL, 1987, pp 39–90, describes encapsulation for controlled drug delivery. See Also, Heller. (2), In: hydrogels in Medicine and Pharmacy, N.A. Peppes ed., Vol. III, CRC press, Boca Raton, Fl, 1987, pp 137–149, describes bioerodible polymers. Heller, *J. of Controlled Release* (1985) 2:167–177; Leong et al., *BioMaterials* (1986) 7:364–371 describes polyanhydride microspheres. Jackanicz et al., *Contraception* (1973) 8:277; Yolles et al., In: Controlled Release of Biologically Active Agents, Tanquary et al. eds, Plenum Press, New York, NY, 1974, Chapter 3; Liu et al., *Opthamology* (1987) 94:1155–1159 and references cited therein report a study for the intravitreal use of liposomes for therapeutic treatment of eye disease. See also, Cutright et al., *Oral surgery, Oral Medicine, and Oral Pathology* (1974) 37:142 and Shindler et al., *Contemporary Topics in Polymer Science* (1977) 2:251–289. Anderson et al., Contraception (1976) 13:375 and Miller et al., *J. Biomed. Materials Res.* (1977) 11:711, describe various properties of poly(dl-lactic acid). U.S. Pat. Nos. of interest include 3,416,530; 3,626,940; 3,828,777; 3,870,791; 3,916,899; 3,944,064; 3,962,414; 4,001,388; 4,052,505; 4,057,619; 4,164,559; 4,179,497; 4,186,184; 4,190,642; 4,281,654; 4,303,637; 4,304,765; 4,304,767; 4,439,198; 4,452,776; 4,474,751; 4,613,330; and 4,617,186.

SUMMARY OF THE INVENTION

Biocompatible, particularly biodegradble, drug containing microencapsulated implants are introduced into the anterior and/or posterior chambers of the eye to provide a therapeutically effective amount of the drug for treatment of an ocular condition. The microcapsules are for the most part polymers, particularly polyesters or ethers.

DESCRIPTION OF THE SPECIFIC EMBODIMENTS

Ocular conditions, diseases and disorders, are treated by introducing slow release drug-containing microcapsules directly into the anterior and/or posterior chambers of the eye. The microcapsules are formulated to include one or more drugs which may be released over an extended period of time at a therapeutically effective dosage into the vitreous humor. In this manner, drug released from microcapsules placed into the anterior chamber will reach the cornea, aqueous humor, trabecular mesh work, iris, lens, and related structures in the anterior chamber. Microcapsules introduced into the posterior chamber are diffused throughout the vitreous in the chamber and into the entire retina (which consists of 10 different layers), into the choroid and the apposed sclera. Thus, the drug will be available at the site(s) where the drug is needed and will be maintained at an effective dosage, rather than rapidly being washed out or as in the case of systemic administration, requiring greatly elevated levels of drug administration to the host to achieve an effective level in the eye.

The primary element of the capsule will be the polymeric encapsulating agent or lipid encapsulating agent. The compositions will be biocompatible, preferably biodegradable.

For the most part, the polymeric compositions will be organic esters or ethers, which when degraded result in physiologically acceptable degradation products, including the monomers. However, anhydrides, amides, orthoesters or the like, by themselves or in combination with other monomers may also find use. The polymers may be addition or condensation polymers, particularly condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g. hydroxy or ether, carbonyl, e.g. non-oxo-carbonyl, such as carboxylic acid ester, and the like. The nitrogen may be present as amide, cynao and amino. The polymers set forth in Heller (1), supra, may find use, and that disclosure is specifically incorporated herein by reference.

Of particular interest are polymers of hydroxyaliphatic carboxylic acids, either homo- or copolymers, and polysaccharides, Included among the polyesters of interest are polymers of D-lactic acid, L-lactic acid, racemic lactic acid, glycolic acid, polycaprolactone, and combinations thereof. By employing the L-lactate, a slowly eroding polymer is achieved, while erosion is substantially enhanced with the lactate racemate.

Among the polysaccharides will be calcium alginate, and functionalized celluloses, particularly carboxymethylcellulose esters characterized by being water insoluble, a molecular weight of about 5 kD to 500 kD, etc. Other polymers of interest include polyvinyl alcohol, esters and ethers, which are biocompatible and may be biodegradable. For the most part, characteristics of the polymers will include biocompatibility, compatibility with the drug, ease of encapsulation, a halflife in the physiological environment of at least 6 hrs, preferably greater than one day, does not significantly enhance the viscosity of the vitreous, water insoluble, and the like.

The biodegradable polymers which form the microencapsulated particles will desirably be subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

By employing a biodegradable polymer, particularly one where the biodegradation is relatively slow, the rate of release of the drug will be primarily diffusion controlled, depending upon the surrounding membrane or monolithic polymer structure, rather than breakdown of the particle. For the most part, the selected particles will have lifetimes at least equal to the desired period of administration, preferably at least twice the desired period of administration, and may have lifetimes of 5 to 10 times the desired period of administration. The period of administration will usually be at least 3 days, more usually at least 7 days, generally at least about 15 days and may be 20 days or more.

The particles may be substantially homogeneous as to composition and physical characterstics or heterogeneous. Thus, particles can be prepared where the center may be of one material and the surface have one or more layers of the same or different composition, where the layers may be cross-linked, of different molecular weight, different density or porosity, or the like. For example, the center could be a polylactate coated with a polylactate-polyglycolate copolymer, so as to enhance the rate of initial degradation. Most ratios of lactate to glycolate employed will be in the range of about 1:0-1. Alternatively, the center could be polyvinyl alcohol coated with polylactate, so that on degradation of the polylactate the center would dissolve and be rapidly washed out of the eye.

Any pharmacologically active agent for which sustained release is desirable may be employed. Desirably, the drug will be sufficiently soluble in the vitreous to be presented at a pharmacologically effective dose. Pharmacologic agents which may find use may be found in U.S. Pat. Nos. 4,474,451, columns 4–6 and 4,327,725, columns 7–8, which disclosures are incorporated herein by reference.

Drugs of particular interest include hydrocortisone (5–20mcg/l as plasma level), gentamycin (6–10mcg/ml in serum), 5-fluorouracil ($\sim$30mg/kg body weight in serum), sorbinil, IL-2, TNF, Phakan-a (a component of glutathione), thioloa-thiopronin, Bendazac, acetylsalicylic acid, trifluorothymidine, interferon ($\alpha$, $\beta$ and $\gamma$), immune modulators, e.g. lymphokines, monokines, and growth factors, etc.

Other drugs of interest include anti-glaucoma drugs, such as the beta-blockers: timolol maleate, betaxolol and metipranolol; mitotics: pilocarpine, acetylcholine chloride, isofluorophate, demacarium bromide, echothiophate iodide, phospholine iodide, carbachol, and physostigimine; epinephrine and salts, such as dipivefrin hydrochloride; and dichlorphenamide, acetazolamide and methazolamide; anti-cataract and anti-diabetic retinopathy drugs, such as aldose reductase inhibitors: tolrestat, lisinopril, enalapril, and statil; thiol cross-linking drugs other than those considered previously; anti-cancer drugs, such as retinoic acid, methotrexate, adriamycin, bleomycin, triamcinoline, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting agents, such as tissue plasminogen activator, urokinase, and streptokinase; anti-tissue damage agents, such as superoxide dismutase; proteins and nucleic acids, such as mono- and polyclonal antibodies, enzymes, protein hormones and genes, gene fragments and plasmids; steriods, particularly antiinflammatory or anti-fibrous drugs, such as cortisone, hydrocortisone, prednisolone, prednisome, dexamethasone, peogesterone-like compounds, medrysone (HMS) and fluorometholone; non-steroidal anti-inflammatory drugs, such as ketrolac tromethamine, dichlofenac sodium and suprofen; antibiotics, such as loridine (cephaloridine), chloramphenicol, clindamycin, amikacin, tobramycin, methicillin, lincomycin, oxycillin, penicillin, amphotericin B, polymyxin B, cephalosporin family, ampicillin, bacitracin, carbenicillin, cepholothin, colistin, erythromycin, streptomycin, neomycin, sulfacetamide, vancomycin, silver nitrate, sulfisoxazole diolamine, and tetracycline; other antipathogens, including anti-viral agents, such as idoxuridine, trifluorouridine, vidarabine (adenine arabinoside), acyclovir (acycloguanosine), pyrimethamine, trisulfapyrimidine-2, clindamycin, nystatin, flucytosine, natamycin, miconazole and piperazie derivatives, e.g. diethylcarbamazine; cycloplegic and mydriatic agents, such as atropine, cyclogel, scopolamine, homatropine and mydriacyl.

Other agents include anticholinergics, anticoagulants, antifibrinolytic agents, antihistamines, antimalarials, antitoxins, chelating agents, hormones, immunosuppressives, thrombolytic agents, vitamines, salts, desensitizing agents, prostaglandins, amino acids, metabolites and antiallergenics.

The amount of drug employed in the capsule will vary widely depending on the effective dosage required and rate of release. Usually the drug will be from about 1 to 80, more usually 20 to 40 weight percent of the microcapsule.

Other agents may be employed in the formulation for a variety of purposes. In addition to the drug agent, buffering agents and preservatives may be employed. The water soluble preservatives include sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from 0.001 to 5% by weight and preferably 0.01 to 2%. Suitable water soluble buffering agents are alkali or alkaline earth, carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent may be as much as 5% on a weight to weight basis of the total composition.

The particles may be of a narrow or broad range in size, normally not exceeding 300 μm, so as to be capable of being administered with an 18 gauge needle. Usually, the particle range will not differ by greater than about 200% of the average particle size, more usually not greater than about 100%. The average particle size will usually be in the range of 5 μm to 2 mm, more usually in the range of 10 μm to 1 mm. In some instances the particles will be selected to have an average diameter in the range of 1–2 mm to provide large depots, while in other instances the particles will have average diameter in the range of about 25–500 μm, to provide smaller depots. The size of the particle can be used to control the rate of release, period of treatment and drug concentration in the eye. In some situations mixtures of particles may be employed employing the same or different pharmacological agent. In this way in a single administration a course of drug treatment may be achieved, where the pattern of release may be greatly varied.

Various techniques may be employed to produce the encapsulated drugs. Useful techniques include solvent-evaporation methods, phase separation methods, interfacial methods and the like.

In preparing the encapsulated drugs, for the most part solvent-evaporation methods will be employed. Towards this end, the preformed rate controlling polymer is dissolved in a volatile substantially waterimmiscible solvent, such as chloroform, methylene chloride, or benzene. Sometimes, the water immiscible solvent will be modified with a small amount of a water-miscible organic cosolvent, particularly an oxygenated solvent, such as acetone, methanol, ethanol, etc. Usually, the water-miscible organic cosolvent will be less than about 40 vol %, usually less than about 25 vol %. The drug may then be added to the polymer-solvent solution. Depending upon the nature of the drug, one may have the drug dispersed in the viscous polymer-solvent mixture or a solid dispersion of drug particles, where the drug will have been pulverized to obtain a fine powder, usually a microfine powder particularly of a size of less than about 1 mm, usually less than about 0.5 mm, and may be about 0.5 μm or smaller.

The amount of polymer employed in the medium will vary with the size of the particle desired, whether additional coatings will be added, the viscosity of the solution, the solubility of the polymer and the like. Usually, the concentration of polymer will be in the range of 10 to 80 weight percent. The ratio of drug to polymer will vary with the desired rate of release, the amount of drug generally varying in the range of 1 to 80 weight percent of the polymer.

The dispersion or solution obtained above is added to a rapidly stirred aqueous solution comprising water and a dispersing agent, which may be a protective colloid. Of particular interest as macromolecular dispersing agents are agents such as poly(vinyl alcohol) (1–5%) or non-ionic detergents, such as Span detergents.

The volume of the organic phase will be smaller than the aqueous phase, generally being in a volume ratio of from about 1:1 to $10^3$ of organic to aqueous phase, and an oil-in-water emulsion is produced. The rate of stirring is selected to produce the appropriate droplet size and stirring is continued throughout the next step.

In the third step, the microencapsulation vessel is closed and a mild vacuum is applied to the system to evaporate the volatile organic solvent. The solvent should be evaporated slowly, since too rapid evaporation results in bubbles and blow holes formed in the microcapsule walls. The rate of evaporation may be determined empirically, using the experience reported in the literature. Usually the vacuum will be in the range of about 3 to 10 mm Hg. After evaporation has been completed, the resulting microcapsules are centrifuged, washed completely with water, collected, e.g., filtration, and drained. Usually, the microcapsules will then be subdivided with sieves to isolate particles of a size range of the desired diameter.

The process may be carried out conveniently at room temperature, but cooling or heating may be employed in specific situations to optimize the process. The ratio of drug to polymer is adjusted to produce optimized compositions, since the final product will normally result in the initial ratio. By manipulating the initial bulk viscosity of the drug-polymer-solvent mixture and of the aqueous dispersing medium, along with the stir rate, production of microcapsules with the desired size may be optimized. Moreover, the composition of dissolved organic solvent and the rate of solvent evaporation can be tested to produce microcapsules with larger or smaller crystals of drug in the microcapsules. For polymers which are hydrolytically sensitive, the microcapsules should not be exposed to the aqueous dispersing medium for excessively long periods during the solvent-evaporation step.

The particle size distribution of each batch of microcapsules will be relatively narrow. However, when desired, the size-fractions may be further refined by a physical separation process such as dry or wet sieving.

In order to define the potential drug-release behavior of the microcapsules in vivo, a weighed sample of microcapsules may be added to a measured volume of a solution containing four parts by weight of ethanol and six parts by weight of deionized water. The mixture is maintained at 37° C. and stirred slowly to maintain the microcapsules suspended. The appearance of the dissolved drug as a function of time may be followed spectrophotometrically until the absorbance becomes constant or until greater than 90% of the drug has been released. The drug concentration after 1 h in the medium is indicative of the amount of free unencapsulated drug in the dose, while the time required for 90% drug to be released is related to the expected duration of action of the dose in vivo. As a general rule, one day of drug release in vitro is approximately equal to 35 days of release in vivo. While release may not be uniform, normally the release will be free of larger fluctuations from some average value which allows for a relatively uniform release.

The microcapsules may be administered into the eye in a variety of ways, including injection, infusion, trocar, etc. Various techniques for introducing materials into the anterior and/or posterior chambers are well known, see, for example, Liu et al., 1987, supra, and references cited therein.

The following examples are offered by way of illustration and not by way of limitation.

EXPERIMENTAL

The appropriate weight of polymer is solubilized with a water immiscible organic volatile solvent, e.g. benzene, methylene chloride or chloroform. The proper amount of drug is added to the polymeric mixture to form a slurry which is mixed to substantial homogeneity. The slurry is then added dropwise to a vessel containing rapidly stirred deionized distilled water in a volume ratio of 1:0.5–1 $\times 10^3$ (organic slurry:water). The water is 2-5 wt % polyvinyl alcohol. The vessel is sealed and a mild vacuum applied slowly to prevent bubbles and blow holes in the microcapsules over a period of about 8-10 hrs. After evaporation of the solvent, the microcapsules are centrifuged, washed repeatedly with sterile distilled water, filtered and drained. The microcapsules are sized with sieves, dried in vacuo and may then be used directly by trocar injection for introduction into the vitreous humor of the eye. For sulfadiazine, the drug was 10 wt %, for hydrocortisone 40 wt %, and for methotrexate 25 wt % of the polymer weight. The drugs were used as microfine powers, $\leq 20$ μm. The trocar injection was with a 20-gauge needle, the particles being of an average size of about 0.2 mm.

The monomer DL-lactic acid was recrystallized twice from acetone and twice from methyl ethyl ketone. The lactic acid was added to a polymerization tube, air and residual solvent removed in vacuo and the tube heated until the lactic acid melted. Catalyst (tetraphenyl tin, 0.02 wt %) was added and the tube sealed in vacuo and heated at 170°-175° C. for seven hours. After cooling, the tube was opened and the polymeric product dissolved in acetone, precipitated with water at room temperature and then dried in vacuo. The polymer should not be exposed to water for long periods of time, particularly during the solventevaporation step during microcapsule formation.

The following tables indicate the results:

TABLE 1

| Drug | | Analysis | Time | | RE | | LE | |
|---|---|---|---|---|---|---|---|---|
| # | ug/ml | | wks | mos | AC | PC | AC | PC |
| 1* | sulfadiazine | fluorescence | 0 | | 0.0 | — | 0 | — |
| | | | 1 | | 2.0 | — | 0 | — |
| | | | 2 | | 1.5 | — | 0 | — |
| | | | 3 | | 1.3 | — | 0 | — |
| | | | 4 | | 1.5 | — | 0 | — |
| | | | 5 | | 1.6 | — | 0 | — |
| | | | 6 | | 1.8 | — | 0 | — |
| | | | 7 | | 1.4 | — | 0 | — |
| | | | 8 | | 1.5 | — | 0 | — |
| | | | 9 | | 1.5 | — | 0 | — |
| | | | 10 | | 1.4 | — | 0 | — |
| | | | 11 | | 1.6 | — | 0 | — |
| | | | 12 | | 1.3 | — | 0 | — |

\# = Animal = Rabbit
\* = Microcapsules in AC (anterior chamber)
\+ = Microcapsules in PC (posterior chamber)

The sulfadiazine containing polylactic microcapsules placed in the anterior chamber of the right eye released the drug for 12 months. There was no detection of any drug in the control left eye.

TABLE 2

| Drug | | Analysis | Time | | RE | | LE | |
|---|---|---|---|---|---|---|---|---|
| # | ug/ml | | wks | mos | AC | PC | AC | PC |
| 2* | sulfadiazine | fluorescence | 0 | | 0.0 | — | 0 | — |
| | | | 1 | | 0 | — | 0.0 | — |
| | | | 2 | | 0 | — | 2.5 | — |
| | | | 3 | | 0 | — | 2.6 | — |
| | | | 4 | | 0 | — | 2.4 | — |
| | | | 5 | | 0 | — | 2.9 | — |
| | | | 6 | | 0 | — | 3.0 | — |
| | | | 7 | | 0 | — | 2.8 | — |
| | | | 8 | | 0 | — | 2.6 | — |
| | | | 9 | | 0 | — | 2.6 | — |
| | | | 10 | | 0 | — | 2.7 | — |
| | | | 11 | | 0 | — | 2.4 | — |
| | | | | 12 | 0 | — | 2.3 | — |

\# = Animal = Rabbit
\* = Microcapsules in AC (anterior chamber)
\+ = Miorocapsules in PC (posterior chamber)

The experiment of Table 1 was repeated, employing a higher dose level.

TABLE 3

| Drug | | Analysis | Time | | RE | | LE | |
|---|---|---|---|---|---|---|---|---|
| # | ug/ml | | wks | mos | AC | PC | AC | PC |
| 3* | sulfadiazine | fluorescence | 0 | | 0.0 | — | — | — |
| | | | 2 | | 3.1 | — | — | — |
| | | | 4 | | 2.9 | — | — | — |
| | | | 6 | | 3.2 | — | — | — |
| | | | 8 | | 3.0 | 0.0 | — | — |

\# = Animal = Rabbit
\* = Microcapsules in AC (anterior chamber)
\+ = Microcapsules in PC (posterior chamber)

A shorter time period was used to monitor the course of the release. The data demonstrate that the drug level had equilibrated within 2 weeks (the 2 week level was the same as the 8 week level). At 8 weeks when the animal was sacrificed, the level in the posterior chamber was found to be 0. The data demonstrate that medication placed in the anterior chamber did not migrate into the posterior chamber.

TABLE 4

| Drug | | Analysis | Time | | RE | | LE | |
|---|---|---|---|---|---|---|---|---|
| # | ug/ml | | wks | mos | AC | PC | AC | PC |
| 4* | sulfadiazine | fluorescence | 0 | | 0.0 | — | — | — |
| | | | 2 | | 4.2 | — | — | — |
| | | | 4 | | 4.3 | 0 | — | — |

\# = Animal = Rabbit
\* = Microcapsules in AC (anterior chamber)
\+ = Microcapsules in PC (posterior chamber)

This experiment repeats the experiment above, but employs a higher dosage level.

TABLE 5

| Drug | | Analysis | Time | | RE | | LE | |
|---|---|---|---|---|---|---|---|---|
| # | ug/ml | | wks | mos | AC | PC | AC | PC |
| 1+ | hydrocortisone succinate | HPLC | 1 | | <.02 | 1.5 | 0 | 0 |
| 2+ | hydrocortisone succinate | HPLC | 2 | | <.02 | 2.0 | 0 | 0 |
| 3+ | hydrocortisone succinate | HPLC | 3 | | <.02 | 2.3 | 0 | 0 |
| 4+ | hydrocortisone succinate | HPLC | 4 | | <.02 | 1.0 | 0 | 0 |
| 5+ | hydrocortisone succinate | HPLC | 5 | | <.02 | 1.5 | 0 | 0 |
| 6+ | hydrocortisone succinate | HPLC | 6 | | <.02 | 1.25 | 0 | 0 |
| 7+ | hydrocortisone succinate | HPLC | 7 | | <.02 | 4.1 | 0 | 0 |
| 8+ | hydrocortisone succinate | HPLC | 8 | | <.02 | 2.5 | 0 | 0 |
| 9+ | hydro- | HPLC | 9 | | <.02 | 1.5 | 0 | 0 |

TABLE 5-continued

| # | Drug ug/ml | Analysis | Time wks | mos | RE AC | PC | LE AC | PC |
|---|---|---|---|---|---|---|---|---|
| 10+ | cortisone succinate hydrocortisone succinate | HPLC | | 10 | <.02 | 2.4 | 0 | 0 |

\# = Animal = Rabbit
\* = Microcapsules in AC (anterior chamber)
\+ = Microcapsules in PC (posterior chamber)

Ten different animals were employed with hydrocortisone succinate as a drug incorporated into polyactic acid. The same amount of drug/polymer was placed into the right eyes of each of the animals. One animal was sacrficed at the end of each of the months indicated to generate the data. The results demonstrate the following: 1) drug placed in the posterior chamber of the eye did not migrate into the anterior chamber in detectable amounts; 2) drug was still being released at 10 months at roughly the equilibration level; 3) the left eyes which were not medicated showed no drug.

TABLE 6

| # | Drug ug/ml | Analysis | Time wks | mos | RE AC | PC | LE AC | PC |
|---|---|---|---|---|---|---|---|---|
| 1+ | MTX | EMIT | 1 | | — | — | <.01 | 1.0 |
| 2+ | MTX | EMIT | 2 | | — | — | <.01 | 0.9 |
| 3+ | MTX | EMIT | 3 | | — | — | <.01 | 1.1 |
| 4+ | MTX | EMIT | 4 | | — | — | <.01 | 1.0 |
| 5+ | MTX | EMIT | 5 | | — | — | <.01 | 1.2 |
| 6+ | MTX | EMIT | 6 | | — | — | <.01 | 0.8 |
| 7+ | MTX | EMIT | 7 | | — | — | <.01 | 0.7 |

\# = Animal = Rabbit
\* = Microcapsules in AC (anterior chamber)
\+ = Microcapsules in PC (posterior chamber)

Methotrexate was incorporated into polylactic acid and the microcapsules placed in the posterior chamber of the left eye. Drug did no appear to migrate to the anterior chamber. Drug was still being released at 7 months.

It is evident from the above results that microcapsules can find effective use internal to the eye chamber for treatment of a wide variety of conditions. The microcapsules provide for continuous administration of a drug over long periods of time, avoiding the need of a patient to administer drugs in much less effective ways, such as topically. In addition, treatments can be achieved by maintaining appropriately therapeutic levels of drugs in the eye, minimizing high concentrations throughout the host system which may have deleterious effects. The drug is retained in the appropriate site, since migration is not observed to other chambers or eyes. Equilibration levels are rapidly achieved and maintained for long periods of time. Furthermore, one or only a few drug administrations may be required for treatments over extended periods of time, reducing the burden on the patient for self-administration, ensuring continued controlled medication, and minimizing the interference with the activities of the patient.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for treating an eye condition which comprises:
    implanting at least one of the anterior or posterior chamber of an eye at least one microencapsulated drug as particles of not greater than about 300 micrometers, said particles comprising said drug and a pharmacologically acceptable biodegradable polymer which is degraded in the eye.

2. A method according to claim 1, wherein said polymer is a condensation polymer.

3. A method according to claim 2, wherein said polymer is a polyester.

4. A method according to claim 3, wherein said polyester comprises an hydroxyaliphatic carboxylic acid monomer.

5. A method according to claim 4, wherein said hydroxyaliphatic carboxylic acid is lactic acid.

6. A method according to claim 1, wherein said particle comprises a pharmacologically acceptable buffering agent.

7. A method according to claim 1, wherein said drug is a cytotoxic agent.

8. A method according to claim 1, wherein said steroid is hydrocortisone or a pharmacologically acceptable ester.

9. A method according to claim 7, wherein said cytotoxic agent is methotrexate.

10. A method according to claim 1, wherein an effective dosage for treatment of said condition is maintained in said chamber for at least one month.

11. A method according to claim 10, wherein said particle is of an average size in the range of 10 to 250 micrometers.

12. A method according to claim 1, wherein said drug is a growth factor.

* * * * *